(12) United States Patent
Mou et al.

(10) Patent No.: US 10,802,010 B2
(45) Date of Patent: Oct. 13, 2020

(54) DEVICE HAVING ACTUATING AND SENSING MODULE

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Hsuan-Kai Chen, Hsinchu (TW); Wei-Ming Lee, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 240 days.

(21) Appl. No.: 16/053,499

(22) Filed: Aug. 2, 2018

(65) Prior Publication Data

US 2019/0056366 A1 Feb. 21, 2019

(30) Foreign Application Priority Data

Aug. 21, 2017 (TW) .............................. 106128267 A

(51) Int. Cl.
*G01N 33/00* (2006.01)
*F04B 43/04* (2006.01)
(Continued)

(52) U.S. Cl.
CPC ...... *G01N 33/007* (2013.01); *B01L 3/502715* (2013.01); *F04B 43/046* (2013.01);
(Continued)

(58) Field of Classification Search
CPC .. G01N 33/007; G01N 29/222; G01N 33/075; G01N 33/0022; F04B 45/047; F04B 43/046; B01L 3/502715
See application file for complete search history.

(56) References Cited

U.S. PATENT DOCUMENTS 9,857,301 B1* 1/2018 Nourbakhsh ...... G01N 33/0062
2013/0284956 A1* 10/2013 Kwon .................. F16K 99/0051
251/65
(Continued)

FOREIGN PATENT DOCUMENTS

CN 1668527 A 9/2005
CN 103808900 A 5/2014
(Continued)

OTHER PUBLICATIONS

Extended European Search Report for European Application No. 18187015.5, dated Oct. 19, 2018.
(Continued)

*Primary Examiner* — David Z Huang
(74) *Attorney, Agent, or Firm* — Birch, Stewart, Kolasch & Birch, LLP

(57) ABSTRACT

A device includes a main body and an actuating and sensing module. A length of the main body is 0.2~6 mm. A width of the main body is 0.1~5.5 mm. A height of the main body is 0.1~2.5 mm. The actuating and sensing module is disposed in the main body. The actuating and sensing module includes a carrier, a sensor, an actuator, a driving-and-transporting controller and a battery. The sensor, the actuator, the driving-and-transporting controller and the battery are disposed on the carrier. The actuator is disposed on one lateral side of the sensor. The actuator has a fluid channel. The actuator is enabled to transport fluid, so that the fluid flows through the fluid channel toward the sensor, and the sensor measures the fluid received therethrough.

19 Claims, 12 Drawing Sheets

(51) Int. Cl.
   *G01N 29/22*   (2006.01)
   *F04B 45/047*   (2006.01)
   *B01L 3/00*   (2006.01)

(52) U.S. Cl.
   CPC ......... *F04B 45/047* (2013.01); *G01N 29/222* (2013.01); *G01N 33/0022* (2013.01); *G01N 33/0075* (2013.01); *B01L 2200/18* (2013.01); *B01L 2300/022* (2013.01); *B01L 2300/0627* (2013.01); *B01L 2300/0887* (2013.01); *B01L 2300/123* (2013.01); *B01L 2400/0439* (2013.01)

(56) References Cited

U.S. PATENT DOCUMENTS

2017/0222123 A1\* 8/2017 Chen .................. F16K 99/0015
2018/0128397 A1\* 5/2018 Lotters ................ F16K 99/0048

FOREIGN PATENT DOCUMENTS

| CN | 205538890 U | 8/2016 |
| CN | 206038594 U | 3/2017 |
| EP | 3203079 A1 | 8/2017 |
| TW | M525446 U | 7/2016 |
| TW | 201643425 A | 12/2016 |
| TW | M540931 U | 5/2017 |
| WO | WO 2010/043268 A1 | 4/2010 |
| WO | WO 2016/182437 A1 | 11/2016 |

OTHER PUBLICATIONS

Lin et al., "Integrated Microfluidics/Electrochemical Sensor System for Monitoring of Environmental Exposures to Lead and Chlorophenols," Biomedical Microdevices, vol. 3, No. 4, Jan. 1, 2001, pp. 331-338.

Pol et al., "Microfluidic lab-on-a-chip platforms for environmental monitoring," Trends in Analytical Chemistry, vol. 95, 2017 (published online Aug. 9, 2017), pp. 62-68.

\* cited by examiner

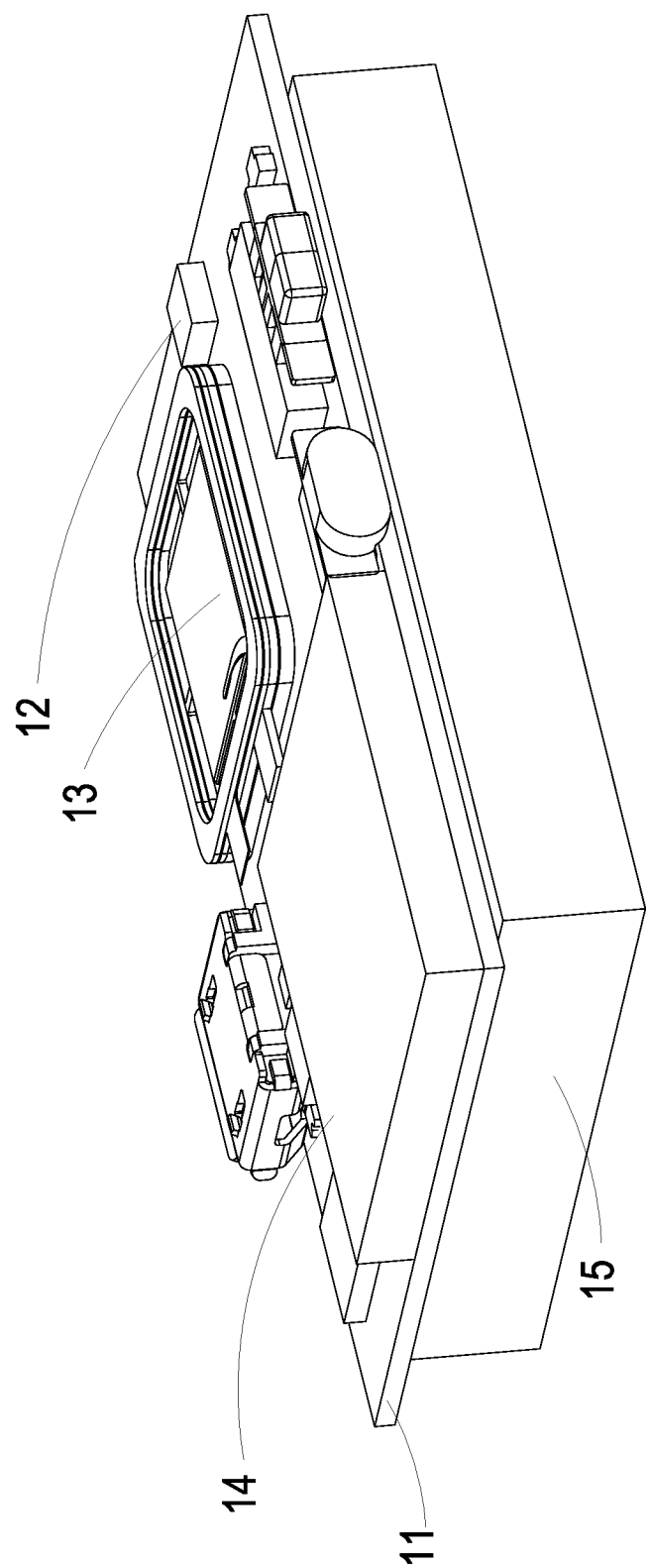

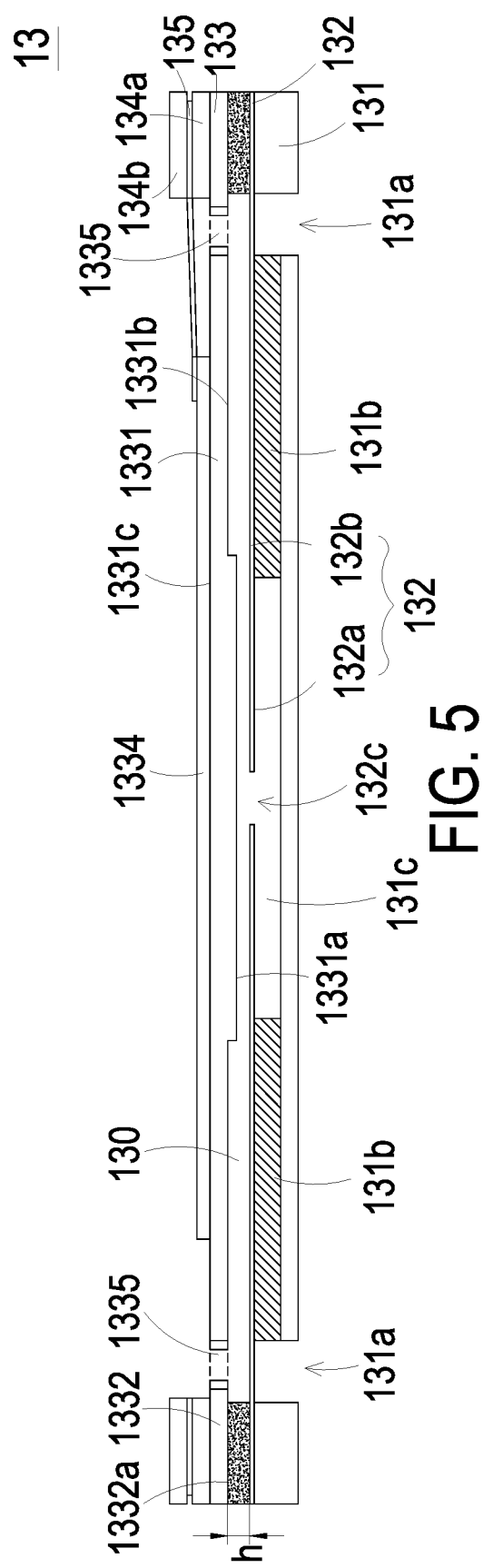
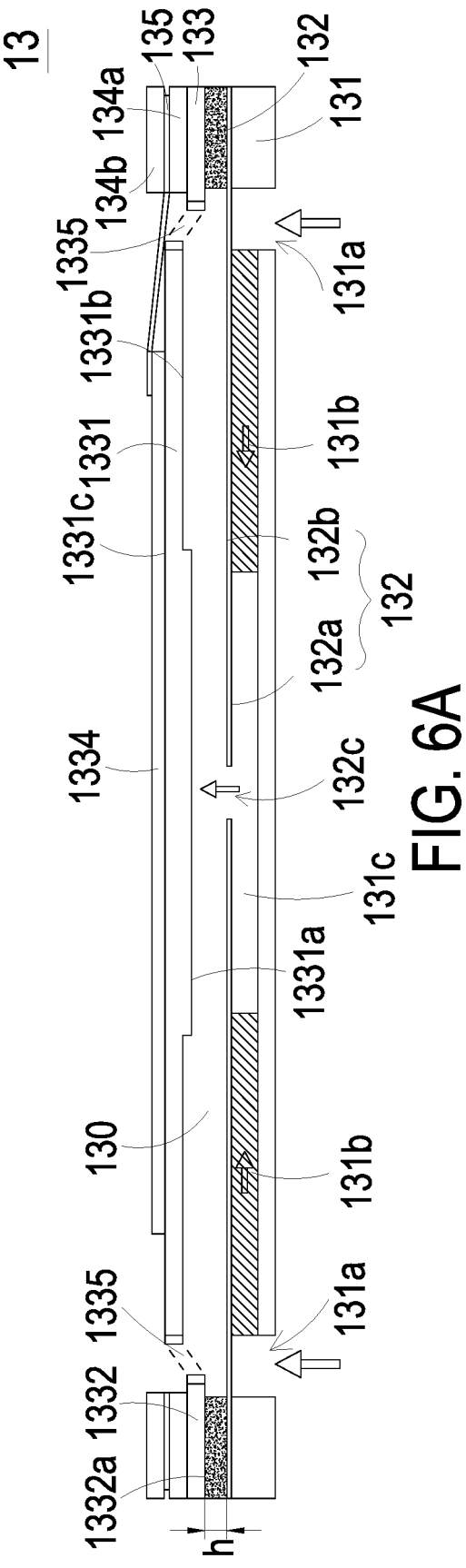
FIG. 5
FIG. 6A

DEVICE HAVING ACTUATING AND SENSING MODULE

FIELD OF THE INVENTION

The present disclosure relates to an electronic device, and more particularly to a device having an actuating and sensing module applicable to an electronic device for monitoring environment.

BACKGROUND OF THE INVENTION

Nowadays, people pay much attention to the air quality in the environment. For example, it is important to monitor carbon monoxide, carbon dioxide, volatile organic compounds (VOC), fine suspended particle (PM2.5), and so on. The exposure of these substances in the environment will cause human health problems or even harm the life. Therefore, it is important for every country to develop and implement the environmental monitoring technology.

As known, portable electronic devices are widely used and applied in the modern lives. In other words, it is feasible to use the portable electronic device to monitor the ambient air. If the portable electronic device is capable of immediately providing people with the monitored information relating to the environment for caution, it may help people escape or prevent from the injuries and influence on human health caused by the exposure of substances described above in the environment. In other words, the portable electronic device is suitably used for monitoring the ambient air in the environment.

Although it is obviously beneficial to make the portable electronic device equipped with sensor for collecting environment data, however, when the sensor is integrated into the electronic device, the monitoring sensitivity and the precision of the sensor should be taken into consideration. For example, the sensor is in contact with the air circulating from the outside and transferred by naturally occurring convection in the surroundings. In other words, the sensor fails to fetch a consistent airflow to maintain stably monitoring. Since it is difficult to trigger response action of the sensor by the circulating air transferred by convection, the response time of the sensor is long and real-time monitoring is not achieved.

Therefore, there is a need of providing a technology of increasing the monitoring accuracy of the sensor and decreasing the response time of the sensor.

SUMMARY OF THE INVENTION

An object of the present disclosure provides a device having an actuating and sensing module. The device includes a main body and at least one actuating and sensing module. The at least one actuating and sensing module is disposed in the main body. The size of the main body is specially designed. The length of the main body is in the range between 0.2 mm and 6 mm, the width of the main body is in the range between 0.1 mm and 5.5 mm, and the height of the main body is in the range between 0.1 mm and 2.5 mm. The ratio of the width to the height is in the range between 0.04 and 55. Consequently, the device is portable.

Another object of the present disclosure provides a device having an actuating and sensing module. The device includes a main body and at least one actuating and sensing module. The at least one actuating and sensing module is disposed in the main body. The actuating and sensing module includes a carrier, at least one sensor, at least one actuator, a driving-and-transporting controller and a battery, which are integrated as a modularized structure. The actuator is used to increase the flow rate of fluid and provide the amount of fluid stably and uniformly. Since the sensor is provided with the amount of the fluid stably and uniformly, the response time of the sensor to the fluid is largely reduced and the fluid is monitored with precision.

A further object of the present disclosure provides a device having an actuating and sensing module. The device is equipped with the actuating and sensing module for monitoring the environment, thereby providing a portable device capable of monitoring the air quality. In other words, the device can monitor the air quality outside the filtering mask and transmit an output data of the monitored data to a connection device. The output data is displayed, stored and transmitted by the connection device. Consequently, the purpose of immediately displaying the output data and issuing the notification signal are achieved. Moreover, the output data can be transmitted to a cloud database. Consequently, the purpose of constructing and managing the data can be achieved. Accordingly, an air quality notification mechanism and an air quality processing mechanism are enabled. Therefore, the user can wear the air-filtering protection device immediately to prevent from the influence on human health caused by the air pollution.

In accordance with an aspect of the present disclosure, a device having actuating and sensing module is provided. The device includes a main body and at least one actuating and sensing module. A length of the main body is in a range between 0.2 mm and 6 mm. A width of the main body is in a range between 0.1 mm and 5.5 mm. A height of the main body is in a range between 0.2 mm and 2.5 mm. The at least one actuating and sensing module is disposed in the main body. The actuating and sensing module includes a carrier, at least one sensor, at least one actuator, a driving-and-transporting controller and a battery. The at least one sensor, the at least one actuator, the driving-and-transporting controller and the battery are disposed on the carrier. The at least one actuator is disposed on one lateral side of the at least one sensor and has at least one fluid channel. The actuator is enabled to transport fluid, so that the fluid flows through the at least one fluid channel toward the at least one sensor, and the at least one sensor measures the fluid received therethrough.

The above contents of the present disclosure will become more readily apparent to those ordinarily skilled in the art after reviewing the following detailed description and accompanying drawings, in which:

BRIEF DESCRIPTION OF THE DRAWINGS

FIG. 2B is a schematic view illustrating the actuating and sensing module of FIG. 2A, in which an actuator and a sensor are disposed in the monitoring chamber;

FIG. 5 is a schematic cross-sectional view illustrating the fluid actuator of the actuating and sensing module as shown in FIGS. 3A and 3B;

FIGS. 6A to 6E schematically illustrate the actions of the fluid actuator of the actuating and sensing module according to the embodiment of the present disclosure.

DETAILED DESCRIPTION OF THE PREFERRED EMBODIMENT

Figure 1A:
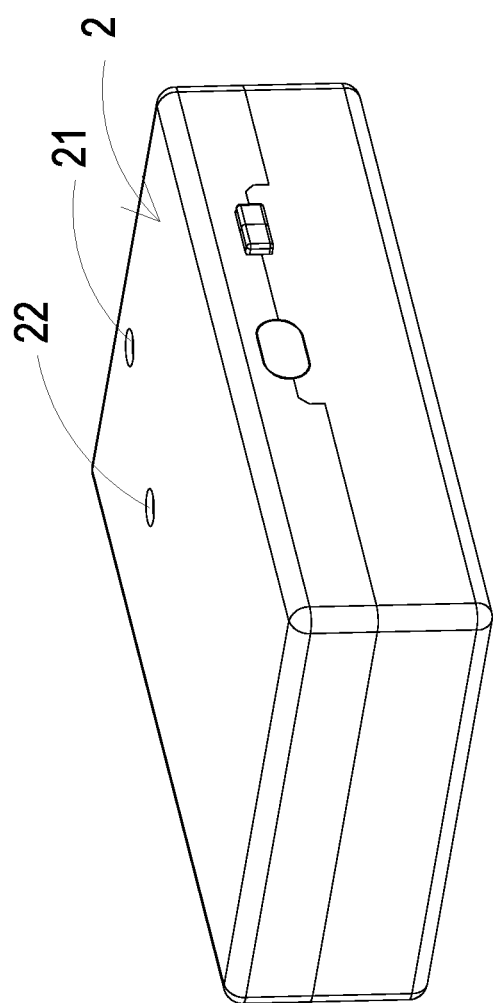
FIG. 1A is a schematic perspective view illustrating the outer appearance of a device having an actuating and sensing module according to an embodiment of the present disclosure.
Figure 1C:
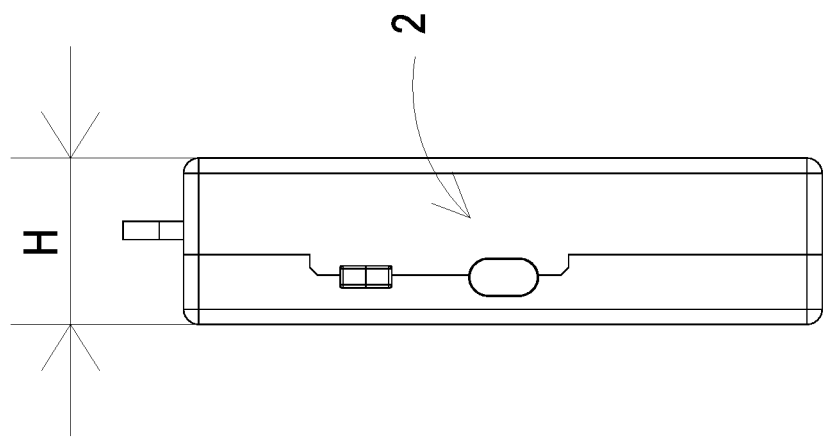
FIG. 1C is a schematic side view illustrating the device having the actuating and sensing module of FIG. 1A.
Figure 1B:
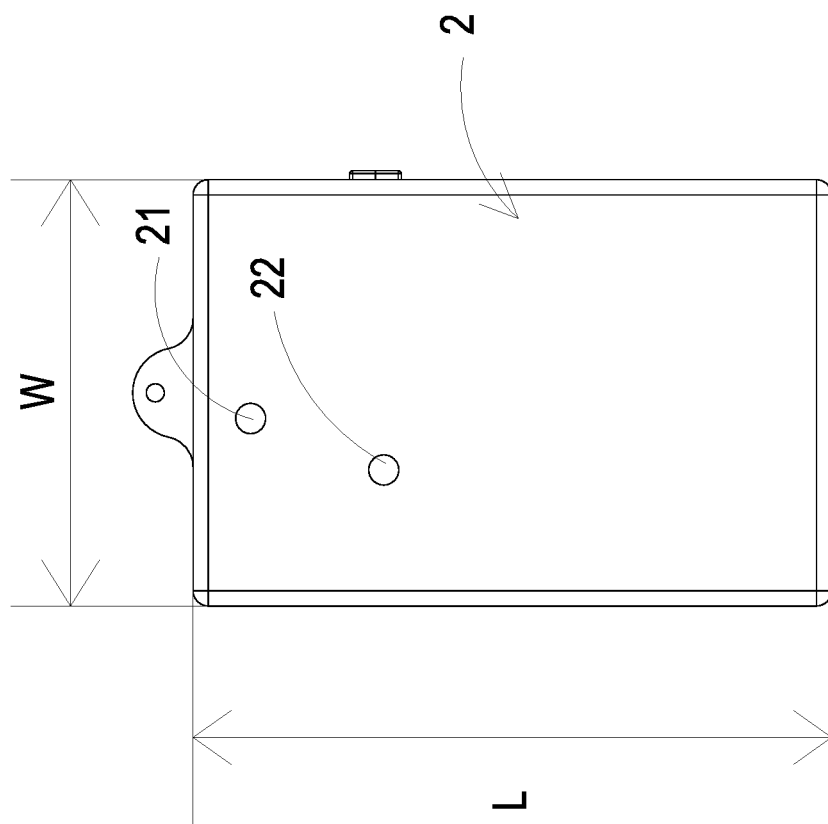
FIG. 1B is a schematic front view illustrating the device having the actuating and sensing module of FIG. 1A.
Figure 2A:
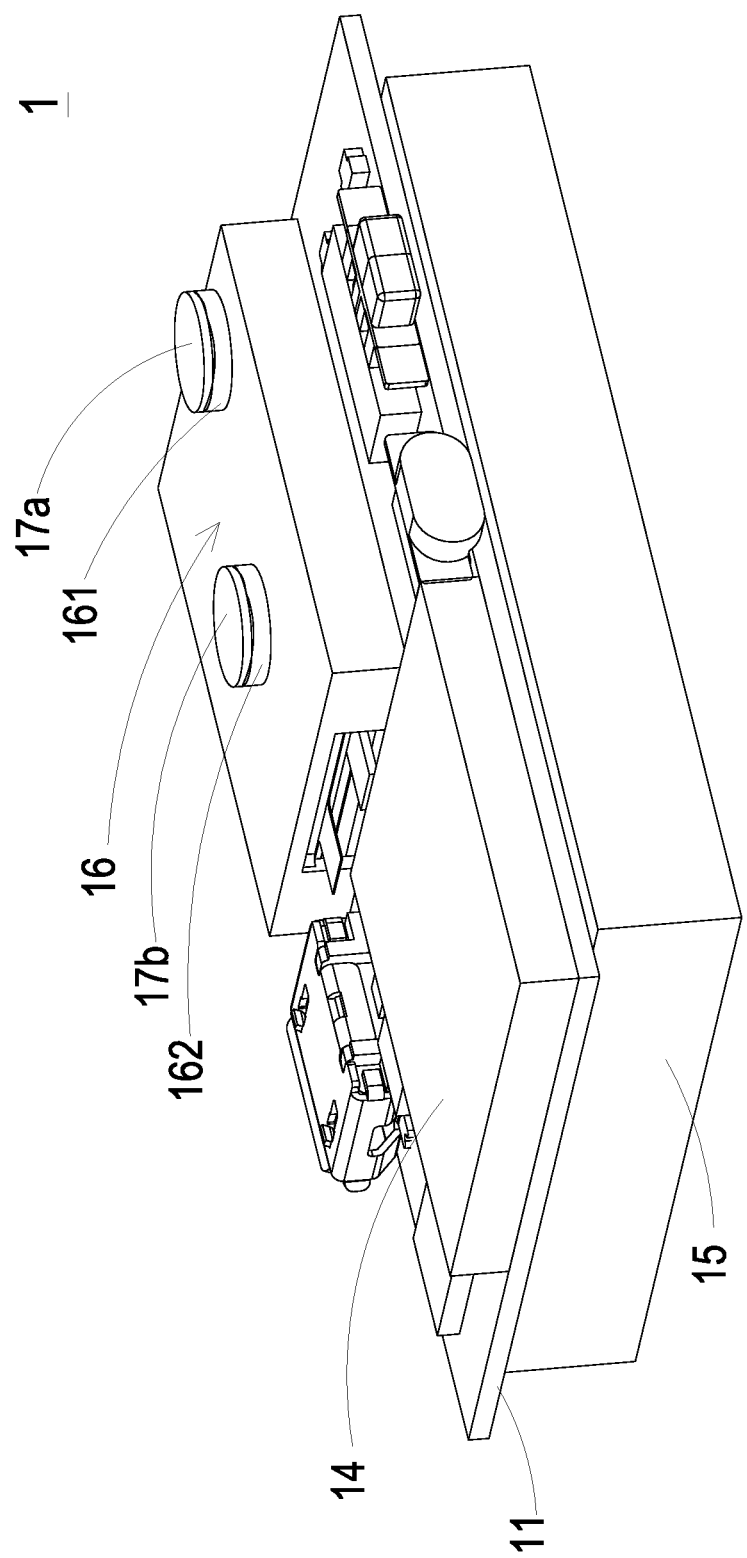
FIG. 2A is a schematic perspective view illustrating the actuating and sensing module of the device according to the embodiment of the present disclosure, in which a monitoring chamber is disposed on the carrier.
Figure 2C:
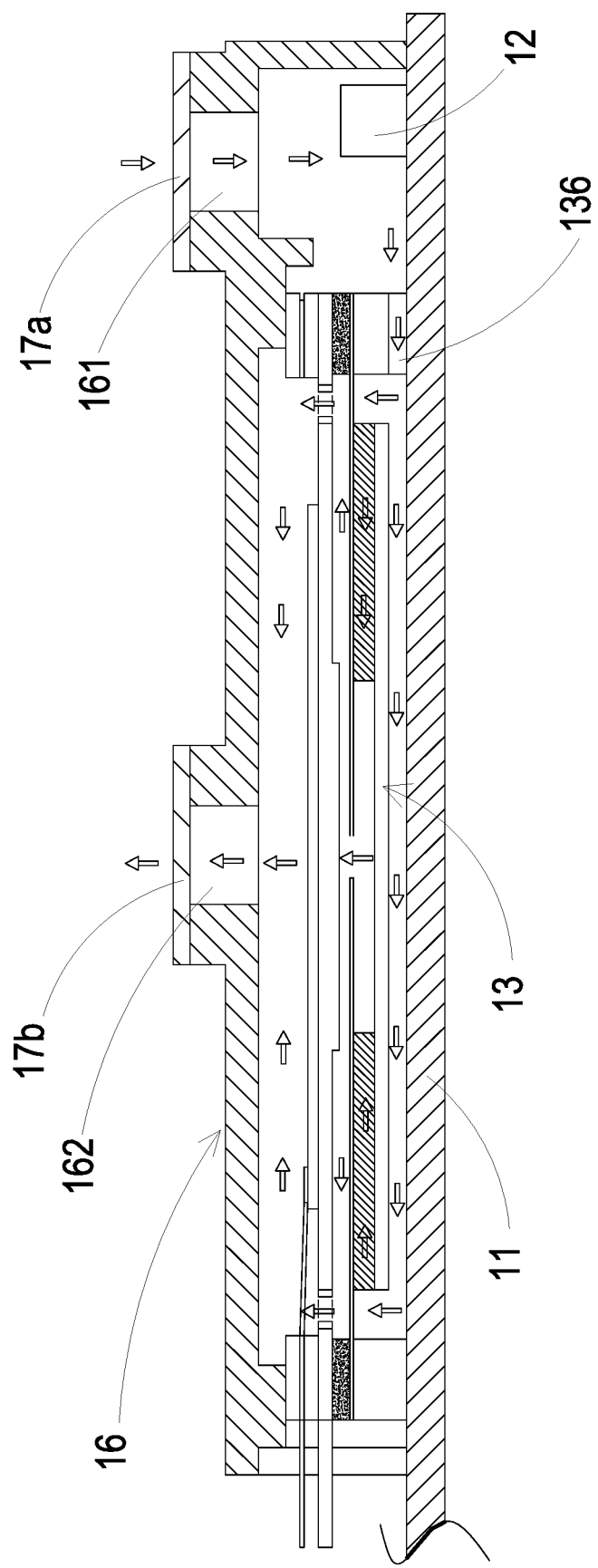
FIG. 2C is a schematic cross-sectional view illustrating the actuating and sensing module of FIG. 2B and the path of the fluid that is guided by the actuating and sensing module of the device according to the embodiment of the present disclosure.

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Please refer to FIGS. 1A to 2C. The present discourse provides a device having actuating and sensing module including at least main body 2, at least one length L, at least one width W, at least one height H, at least one actuating and sensing module 1, at least one carrier 11, at least one sensor 12, at least one actuator 13, at least one driving-and-transporting controller 14, at least one battery 15, at least one fluid channel 136 and at least one fluid. The number of the main body 2, the length L, the width W, the height H, the carrier 11, the driving-and-transporting controller 14, the battery 15 and the fluid is exemplified by one for each in the following embodiments but not limited thereto. It is noted that each of the main body 2, the length L, the width W, the height H, the carrier 11, the driving-and-transporting controller 14, the battery 15 and the fluid can also be provided in plural numbers.

Please refer to FIGS. 1A, 1B, 1C, 2A, 2B and 2C. The present disclosure provides the device including a main body 2 and an actuating and sensing module 1. The actuating and sensing module 1 is disposed in the main body 2 and includes a carrier 11, at least one sensor 12, at least one actuator 13, a driving-and-transporting controller 14 and a battery 15. The main body 2 is a hollow casing with an intake opening 21 and a discharge opening 22.

In order to make the device miniature and portable, minimizing the entire volume and weightiness of the main body 2 is to be considered. For miniaturizing the main body 2, the sizes of the modules disposed within the main body 2 should be minimized. Therefore, the components of the actuating and sensing module 1 also need to be miniaturized. The sensor 12, the driving-and-transporting controller 14 and the battery 15 of the actuating and sensing module 1 are electronic components which have miniature sizes. However, the actuator 13 is a driving device with several internal chambers which are to implement actuation and vibration when the actuator 13 is operating. The requirement of such structure of the actuator 13 limits the volume and size thereof. In order to match the size and volume of a current most miniaturized actuator, the size of the main body 2 is specially designed as follows so as to achieve optimal miniaturization: the length L of the main body 2 is in the range between 0.2 mm and 6 mm, the width W of the main body 2 is in the range between 0.1 mm and 5.5 mm, and the height H of the main body 2 is in the range between 0.1 mm and 2.5 mm. In some embodiments, the ratio of the width W to the height H is in the range between 0.04 and 55. The main body 2 under this condition is miniaturized and thin, so that the device to which the main body 2 is applied can be portable.

Please refer to FIGS. 2A, 2B and 2C again. The carrier 11 of the actuating and sensing module 1 is a platform for integrating the sensor 12, the actuator 13, the driving-and-transporting controller 14 and the battery 15. In an embodiment, the carrier 11 is a substrate such as a printed circuit board (PCB). An array of the sensor 12 and the actuator 13 is disposed on the carrier 11. It should be noted that the example of the carrier 11 is not restricted, and the carrier 11 can be other platform for supporting and integrating the sensor 12 and the actuator 13. In an embodiment, the actuating and sensing module 1 further includes a monitoring chamber 16. The sensor 12 and the actuator 13 are disposed in the monitoring chamber 16. The monitoring chamber 16 includes an inlet passage 161 and an outlet passage 162. When the actuating and sensing module 1 is disposed in the main body 2, the inlet passage 161 is substantially aligned with the intake opening 21 of the main body 2 to be in fluid communication therewith, and the outlet passage 162 is substantially aligned with the discharge opening 22 of the main body 2 to be in fluid communication therewith. The openings formed by the inlet passage 161 and the outlet passage 162 on an external surface outside the monitoring chamber 16 are covered by two protective films 17a, 17b, respectively. As so, the two protective films 17a, 17b are also substantially aligned with the intake opening 21 and the discharge opening 22 of the main body 2, respectively. The protective films 17a, 17b may be waterproof and dustproof film structures, in which only the gas is permitted to pass therethrough. Consequently, the fluid introduced into the inlet passage 161 is filtered by the protective film 17a, and the fluid discharged through the outlet passage 162 is filtered by the protective film 17b, in a waterproof and dustproof manner.

In some embodiments, the sensor 12 is disposed on the carrier 11 and substantially in alignment with the inlet passage 161. The actuator 13 is substantially aligned with the outlet passage 162. The actuator 13 is disposed on one lateral side of the sensor 12. After the actuator 13 is disposed on the carrier 11, the at least one fluid channel 136 is arranged between the actuator 13 and the carrier 11. When the actuator 13 is enabled, the fluid is driven to flow in the direction indicated by the arrows (see FIG. 2C). At this moment, the drainage occurs in the fluid channel 136 to make the ambient fluid guided in the inlet passage 161 and passes through the sensor 12. The sensor 12 measures the received fluid. Moreover, since the inner structure of the actuator 13 is capable of guiding the fluid to flow stably and uniformly, the sensor 12 receives a stable and uniform flow of the fluid and directly measures the fluid. Under this circumstance, the response time of the sensor 12 to the fluid is reduced and the fluid is monitored with precision.

An example of the sensor 12 includes but is not limited to a temperature sensor, a volatile organic compound sensor (e.g., a sensor for measuring formaldehyde or ammonia gas), a particulate sensor (e.g., a fine suspended particle (PM2.5) sensor), a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, or the combination thereof. Alternatively, the sensor 20 may be a bacterial sensor, a virus sensor, a microorganism sensor, or a combination thereof.

The actuator 13 is a driving device capable of driving a controlled system in response to a control signal. The actuator 13 includes but is not limited to an electric actuator, a magnetic actuator, a thermal actuator, a piezoelectric actuator, a fluid actuator, and a combination thereof. For example, the electric actuator is a DC motor, an AC motor or a step motor, the magnetic actuator is a magnetic coil motor, the thermal actuator is a heat pump, the piezoelectric actuator is a piezoelectric pump, and the fluid actuator is a gas pump or a liquid pump.

In the present embodiment, the actuator 13 of the actuating sensing module 1 is a fluid actuator. The actuator 13 is referred to as the fluid actuator 13 hereinafter for detailed illustration. The fluid actuator 13 may be a driving structure of a piezoelectric actuating pump, or a driving structure of a micro-electro-mechanical system (MEMS) pump. In the following description, the actions of the fluid actuator 13 are exemplified by a piezoelectric pump.

Figure 3A:
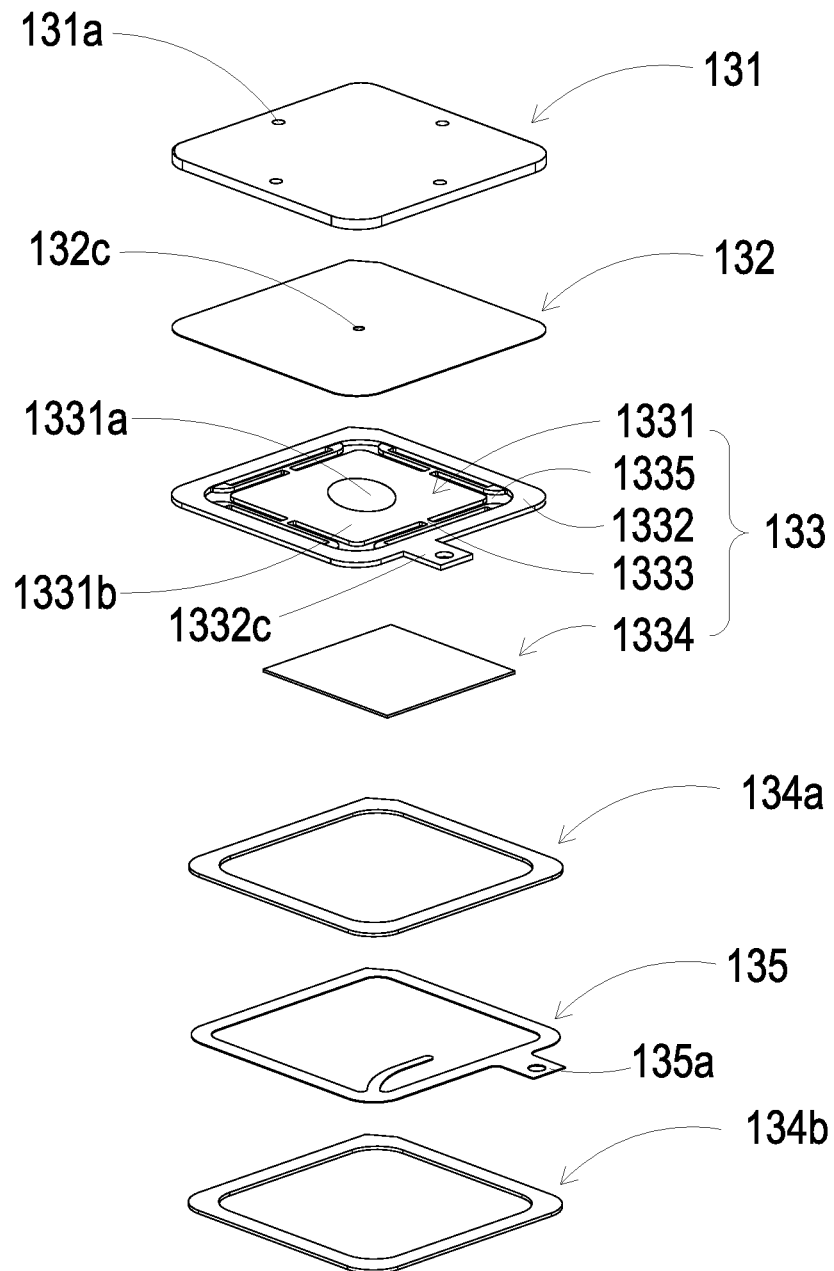
FIG. 3A is a schematic exploded view illustrating a fluid actuator used in the actuating and sensing module of the device according to the embodiment of the present disclosure.
Figure 3B:
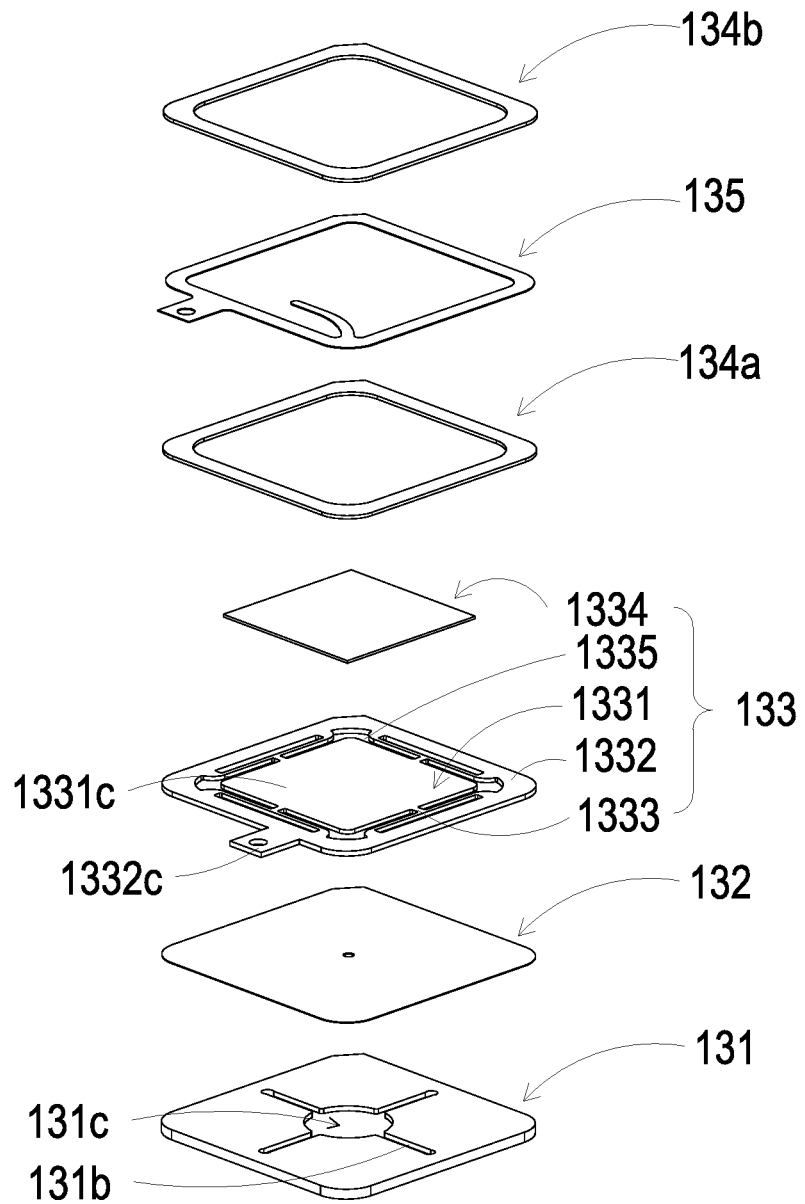
FIG. 3B is a schematic exploded view illustrating the fluid actuator of FIG. 3A and taken along another viewpoint.

Please refer to FIGS. 3A and 3B. The fluid actuator 13 includes a fluid inlet plate 131, a resonance plate 132, a piezoelectric actuating member 133, a first insulation plate 134a, a conducting plate 135 and a second insulation plate 134b. The piezoelectric actuating member 133 is facing the resonance plate 132. The fluid inlet plate 131, the resonance plate 132, the piezoelectric actuating member 133, the first insulation plate 134a, the conducting plate 135 and the second insulation plate 134b are stacked on each other sequentially. After the above components are combined together, the cross-sectional view of the resulting structure of the fluid actuator 13 is shown in FIG. 5.

In the embodiment, the fluid inlet plate 131 has at least one inlet 131a. Preferably but not exclusively, the fluid inlet plate 131 has four inlets 131a. The inlets 131a run through the fluid inlet plate 131. In response to the action of the atmospheric pressure, the fluid can be introduced into the fluid actuator 13 through the at least one inlet 131a. Moreover, at least one convergence channel 131b is formed on a surface of the fluid inlet plate 131 to be spatially corresponding to the at least one inlet 131a on another surface of the fluid inlet plate 131. Preferably but not exclusively, the fluid inlet plate 131 has four convergence channels 131b. Moreover, a central cavity 131c is located at the junction of the convergence channels 131b and in communication with the convergence channels 131b. Therefore, the fluid entered by the at least one inlet 131a would be introduced into the at least one convergence channel 131b and guided to the central cavity 131c, so that the fluid is to be transferred. In this embodiment, the at least one inlet 131a, the at least one convergence channel 131b and the central cavity 131c of the fluid inlet plate 131 are integrally formed from a single structure. The central cavity 131c defines a convergence chamber for temporarily storing the fluid. In some embodiments, the fluid inlet plate 131 may be, for example, made of stainless steel. Moreover, the depth of the convergence chamber defined by the central cavity 131c is equal to the depth of the at least one convergence channel 131b. The resonance plate 132 is made of a flexible material. The resonance plate 132 has a central aperture 132c spatially corresponding to the central cavity 131c of the fluid inlet plate 131 to allow the fluid to flow therethrough. In other embodiments, the resonance plate 132 may be made of copper, but not limited thereto.

The piezoelectric actuating member 133 includes a suspension plate 1331, an outer frame 1332, at least one bracket 1333 and a piezoelectric plate 1334. The piezoelectric plate 1334 is attached on a first surface 1331c of the suspension plate 1331. In response to an applied voltage, the piezoelectric plate 1334 would be subjected to a deformation. When the piezoelectric plate 1334 is subjected to the deformation, it facilitates a bending vibration of the suspension plate 1331. In this embodiment, the at least one bracket 1333 is connected between the suspension plate 1331 and the outer frame 1332, while the two ends of the bracket 1333 are connected with the outer frame 1332 and the suspension plate 1331, respectively, so that the suspension plate 1331 is elastically supported by the bracket 1333. At least one vacant space 1335 is formed among the bracket 1333, the suspension plate 1331 and the outer frame 1332. The at least one vacant space 1335 is in communication with a fluid channel and allows the fluid to go therethrough. It has to be emphasized that the type of the suspension plate 1331 and the outer frame 1332 and the type and the number of the at least one bracket 1333 may be varied according to the practical requirements. The outer frame 1332 is arranged around the suspension plate 1331. Moreover, a conducting pin 1332c may be protruded outwardly from the outer frame 1332 for electrical connection.

Figure 4:
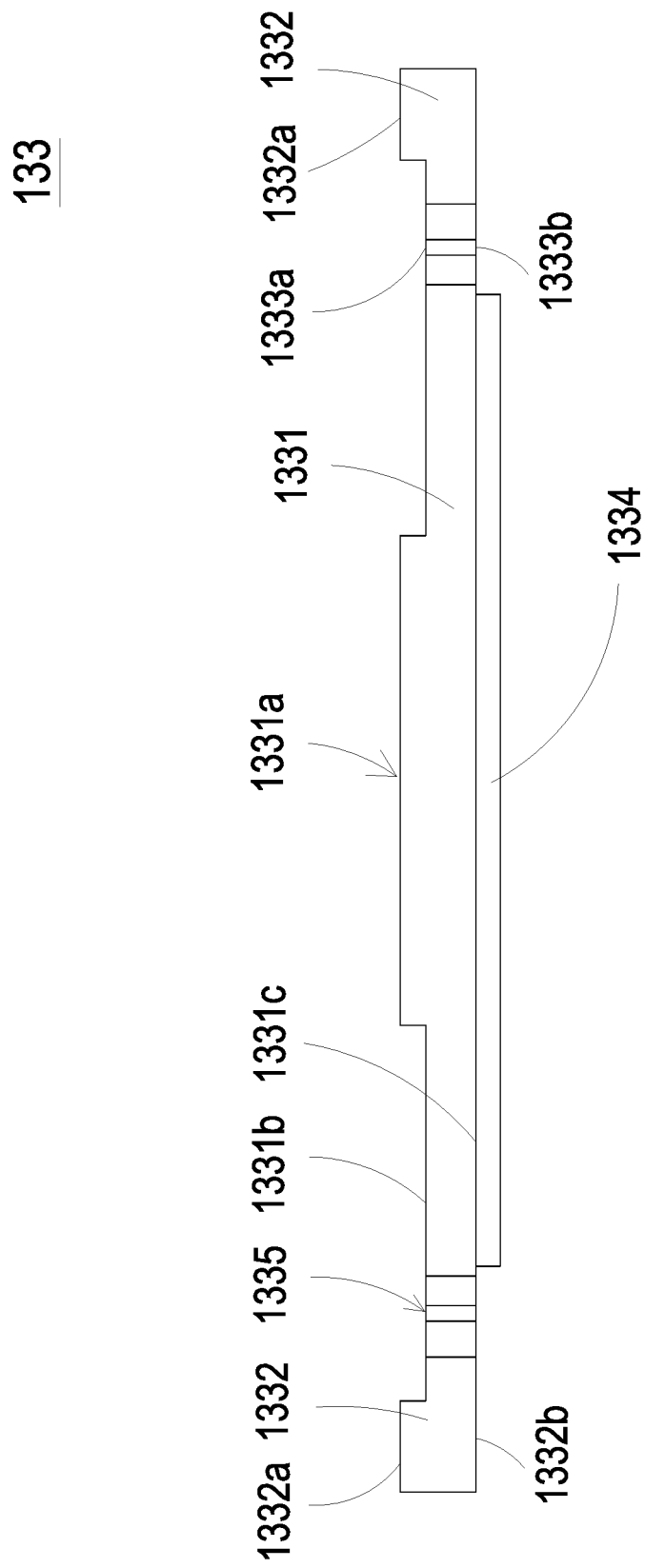
FIG. 4 is a schematic cross-sectional view illustrating the piezoelectric actuating member of the fluid actuator as shown in FIGS. 3A and 3B.

FIG. 4 is a schematic cross-sectional view illustrating a piezoelectric actuating member of the fluid actuator of FIGS. 3A and 3B. As shown in FIG. 4, the suspension plate 1331 has a bulge 1331a that makes the suspension plate 1331 a stepped structure. The bulge 1331a is formed on a second surface 1331b of the suspension plate 1331. The bulge 1331a can be for example but not limited to a circular convex structure. A top surface of the bulge 1331a of the suspension plate 1331 is coplanar with a second surface 1332a of the outer frame 1332, while the second surface 1331b of the suspension plate 1331 is coplanar with a second surface 1333a of the bracket 1333. Moreover, there is a drop of specified amount from the bulge 1331a of the suspension plate 1331 and the second surface 1332a of the outer frame 1332 to the second surface 1331b of the suspension plate 1331 and the second surface 1333a of the bracket 1333. A first surface 1331c of the suspension plate 1331, a first surface 1332b of the outer frame 1332 and a first surface 1333b of the bracket 1333 are coplanar with each other. The piezoelectric plate 1334 is attached on the first surface 1331c of the suspension plate 1331. In some other embodiments, the suspension plate 1331 may be a square plate structure with two flat surfaces, but the type of the suspension plate 1331 may be varied according to the practical requirements. In this embodiment, the suspension plate 1331, the at least one bracket 1333 and the outer frame 1332 may be integrally formed from a metal plate, which can be for example but not limited to a stainless steel material. In an embodiment, the length of a side of the piezoelectric plate 1334 is smaller than the length of a side of the suspension plate 1331. In another embodiment, the length of a side of the piezoelectric plate 1334 is equal to the length of a side of the suspension plate 1331. Similarly, the piezoelectric plate 1334 is a square plate structure corresponding to the suspension plate 1331 in terms of the design.

Please refer to FIG. 3A. In this embodiment, the fluid actuator 13 includes the first insulation plate 134*a*, the conducting plate 135 and the second insulation plate 134*b*, which are stacked on each other sequentially and located under the piezoelectric actuating member 133. The profiles of the first insulation plate 134*a*, the conducting plate 135 and the second insulation plate 134*b* substantially match the profile of the outer frame 1332 of the piezoelectric actuating member 133. In some embodiments, the first insulation plate 134*a* and the second insulation plate 134*b* are made of an insulating material, for example but not limited to a plastic material, so as to provide insulating efficacy. In other embodiments, the conducting plate 135 may be made of an electrically conductive material, for example but not limited to a metallic material, so as to provide electrically conducting efficacy. In this embodiment, the conducting plate 135 may have a conducting pin 135*a* disposed thereon so as to provide the function of electrical connection.

Please refer to FIG. 5. FIG. 5 is a schematic cross-sectional view of the actuator according to the embodiment of the present disclosure. In an embodiment, the fluid inlet plate 131, the resonance plate 132, the piezoelectric actuating member 133, the first insulation plate 134*a*, the conducting plate 135 and the second insulation plate 134*b* of the fluid actuator 13 are stacked on each other sequentially. Moreover, there is a gap h between the resonance plate 132 and the outer frame 1332 of the piezoelectric actuating member 133. In this embodiment, the gap h between the resonance plate 132 and the outer frame 1332 of the piezoelectric actuating member 133 may be peripherally filled with a filler, for example but not limited to a conductive adhesive, so that a depth from the resonance plate 132 to the bulge 1331*a* of the suspension plate 1331 of the piezoelectric actuating member 133 can be maintained. The gap h ensures the proper distance between the resonance plate 132 and the bulge 1331*a* of the suspension plate 1331 of the piezoelectric actuating member 133, so that the fluid can be transferred quickly and the contact interference is reduced, by which the generated noise is largely reduced. In some embodiments, alternatively, the height of the outer frame 1332 of the piezoelectric actuating member 133 is increased, so that the gap is formed between the resonance plate 132 and the piezoelectric actuating member 133, but the present disclosure is not limited thereto.

Please refer to FIG. 3A, FIG. 3B and FIG. 5. After the fluid inlet plate 131, the resonance plate 132 and the piezoelectric actuating member 133 are combined together, a movable part 132*a* and a fixed part 132*b* of the resonance plate 132 are defined. The convergence chamber for converging the fluid is defined by the movable part 132*a* of the resonance plate 132 and the fluid inlet plate 131 collaboratively. Moreover, a first chamber 130 is formed between the resonance plate 132 and the piezoelectric actuating member 133 for temporarily storing the fluid. Through the central aperture 132*c* of the resonance plate 132, the first chamber 130 is in communication with the central cavity 131*c* of the fluid inlet plate 131. The peripheral regions of the first chamber 130 are in communication with the fluid channel through the vacant space 1335 between the brackets 1333 of the piezoelectric actuating member 133.

Please refer to FIGS. 3A, 3B, 5 and 6A to 6B. FIGS. 6A to 6E are cross-sectional views illustrating processing actions of the actuator of the actuating and sensing module according to an embodiment of the present disclosure.

Figure 6B:
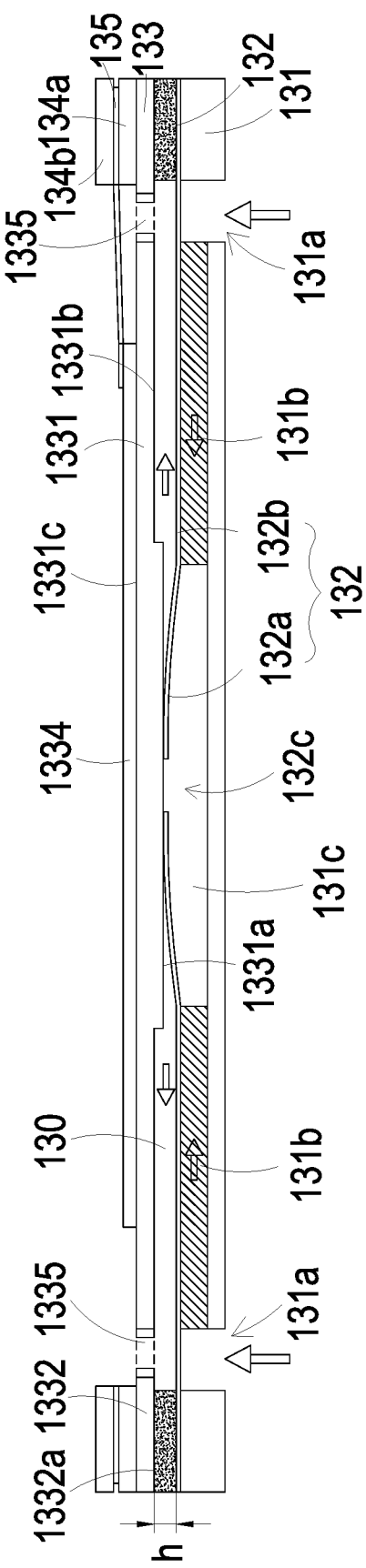
Figure 6C:
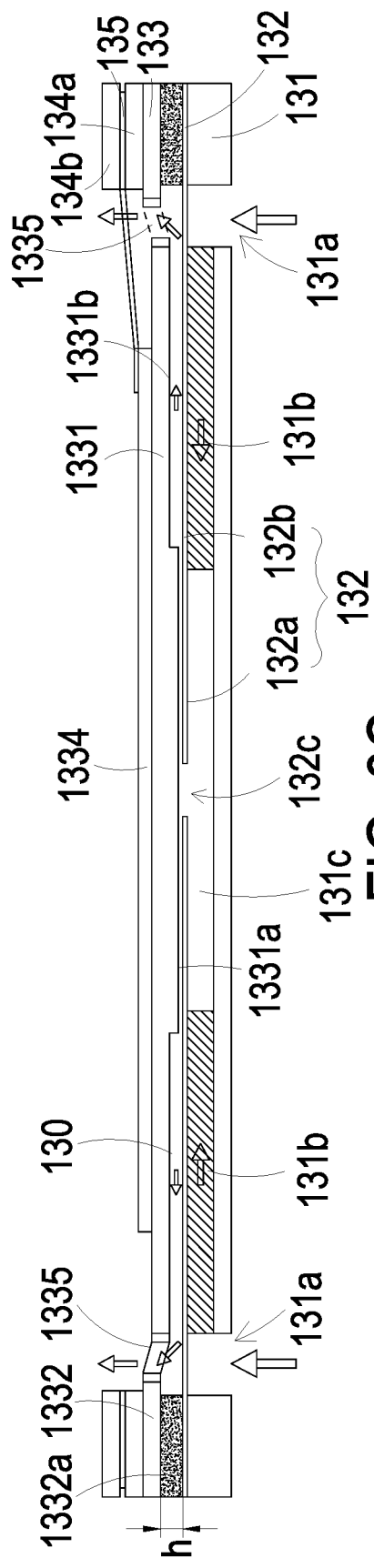
Figure 6D:
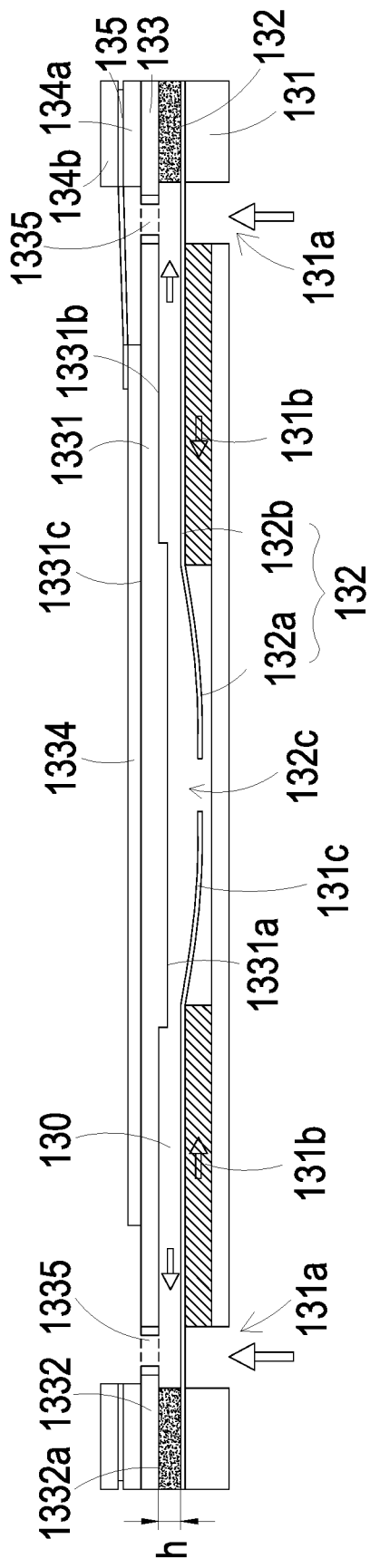
Figure 6E:
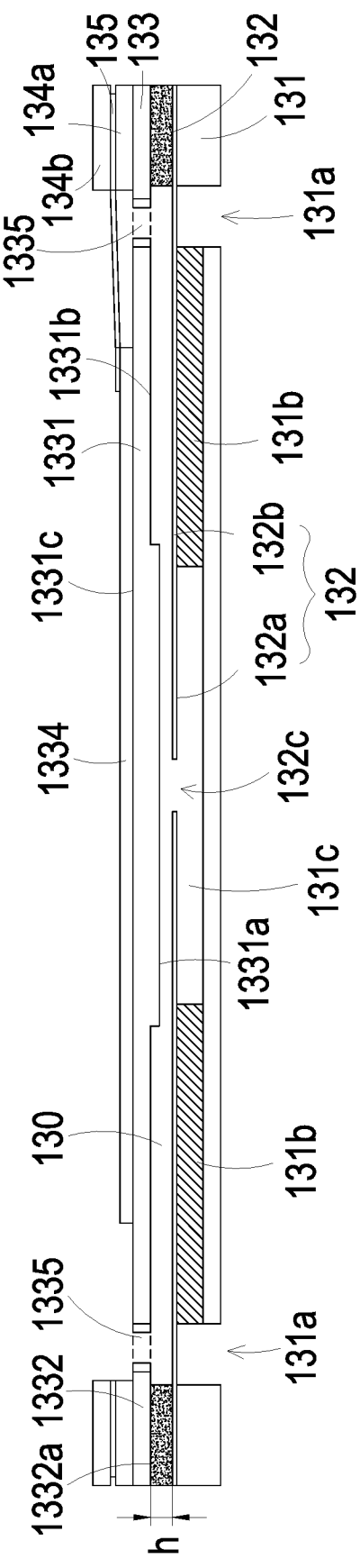

Please refer to FIG. 3A, FIG. 3B, FIG. 5 and FIGS. 6A to 6E. The actions of the fluid actuator 13 will be described as follows. When the fluid actuator 13 is enabled, the piezoelectric actuating member 133 vibrates along a vertical direction in a reciprocating manner by using the bracket 1333 as a fulcrum. Please refer to FIG. 6A, the piezoelectric actuating member 133 vibrates downwardly in response to the applied voltage. Since the resonance plate 132 is light and thin, the resonance plate 132 vibrates along the vertical direction in resonance with the piezoelectric actuating member 133. More especially, a region of the resonance plate 132 spatially corresponding to the central cavity 131*c* of the fluid inlet plate 131 is also subjected to a bending deformation. The region of the resonance plate 132 corresponding to the central cavity 131*c* of the fluid inlet plate 131 is the movable part 132*a* of the resonance plate 132. When the piezoelectric actuating member 133 vibrates downwardly, the movable part 132*a* of the resonance plate 132 is subjected to the bending deformation because the movable part 132*a* of the resonance plate 132 is pushed by the fluid and vibrates in response to the piezoelectric actuating member 133. In response to the downward vibration of the piezoelectric actuating member 133, the fluid is fed into the at least one inlet 131*a* of the fluid inlet plate 131. Then, the fluid is transferred to the central cavity 131*c* of the fluid inlet plate 131 through the at least one convergence channel 131*b*. Then, the fluid is transferred through the central aperture 132*c* of the resonance plate 132 spatially corresponding to the central cavity 131*c*, and introduced downwardly into the first chamber 130. As the piezoelectric actuating member 133 is enabled, the resonance of the resonance plate 132 occurs. Consequently, the resonance plate 132 vibrates along the vertical direction in the reciprocating manner. As shown in FIG. 6B, during the vibration of the movable part 132*a* of the resonance plate 132 at this stage, the movable part 132*a* of the resonance plate 132 moves down to contact and attach on the bulge 1331*a* of the suspension plate 1331 of the piezoelectric actuating member 133, and a distance from the fixed part 132*b* of the resonance plate 132 to a region of the suspension plate 1331 except the bulge 1331*a* remains the same. Owing to the deformation of the resonance plate 132 described above, a middle communication space of the first chamber 130 is closed, and the volume of the first chamber 130 is compressed. Under this circumstance, the pressure gradient occurs to push the fluid in the first chamber 130 moving toward peripheral regions of the first chamber 130 and flowing downwardly through the vacant space 1335 of the piezoelectric actuating member 133. Referring to FIG. 6C, the movable part 132*a* of the resonance plate 132 has returned to its original position when the piezoelectric actuating member 133 vibrates upwardly. Consequently, the volume of the first chamber 130 is continuously compressed to generate the pressure gradient which makes the fluid in the first chamber 130 continuously pushed toward peripheral regions. Meanwhile, the fluid is continuously fed into the at least one inlet 131*a* of the fluid inlet plate 131, and transferred to the central cavity 131*c*. Then, as shown in FIG. 6D, the resonance plate 132 moves upwardly, which is cause by the resonance of the upward motion of the piezoelectric actuating member 133. That is, the movable part 132*a* of the resonance plate 132 is also vibrated upwardly. Consequently, it decreases the flow of the fluid from the at least one inlet 131*a* of the fluid inlet plate 131 into the central cavity 131*c*. At last, as shown in FIG. 6E, the movable part 132*a* of the resonance plate 132 has returned to its original position. As the embodiments described above, when the resonance plate 132 vibrates along the vertical direction in the reciprocating manner, the gap h between the resonance plate 132 and the piezoelectric actuating member 133 is helpful to increase the maximum displacement along the vertical direction during the vibration. In other words, the configuration of the gap h between the resonance plate 132 and the piezoelectric actuating member 133 can increase the amplitude of vibration of the resonance plate 132. Consequently, a pressure gradient is generated in the fluid channels of the fluid actuator 13 to facilitate high speed flow of the fluid. Moreover, since there is an impedance difference between the feeding direction and the exiting direction, the fluid can be transmitted from the inlet side to the outlet side. Even if a gas pressure exists at the outlet side, the fluid actuator 13 still has the capability of pushing the fluid to the fluid channel while achieving the silent efficacy. The steps of FIGS. 6A to 6E may be done repeatedly. Consequently, the ambient fluid is transferred by the fluid actuator 13 from the outside to the inside.

After the fluid inlet plate 131, the resonance plate 132, the piezoelectric actuating member 133, the first insulation plate 134a, the conducting plate 135 and the second insulation plate 134b are stacked on each other sequentially, the fluid actuator 13 is assembled. After the fluid actuator 13 is disposed on the carrier 11, the at least one fluid channel 136 (see FIG. 2C) is arranged between the fluid actuator 13 and the carrier 11. The fluid channel 136 is disposed on one lateral side of the sensor 12. When the fluid actuator 13 is enabled, the fluid flows in the direction indicated by the arrows (see FIG. 2C). At this moment, the drainage occurs in the fluid channel 136 so that the ambient fluid is guided in the inlet passage 161 and passes through the sensor 12. The sensor 12 measures the received fluid. Moreover, since the inner structure of the fluid actuator 13 is capable of guiding the fluid to flow stably and uniformly, the sensor 12 receives a stable and uniform flow of the fluid and directly measures the fluid. Under this circumstance, the response time of the sensor 12 to the fluid is reduced, and the fluid is monitored with precision.

Figure 7:
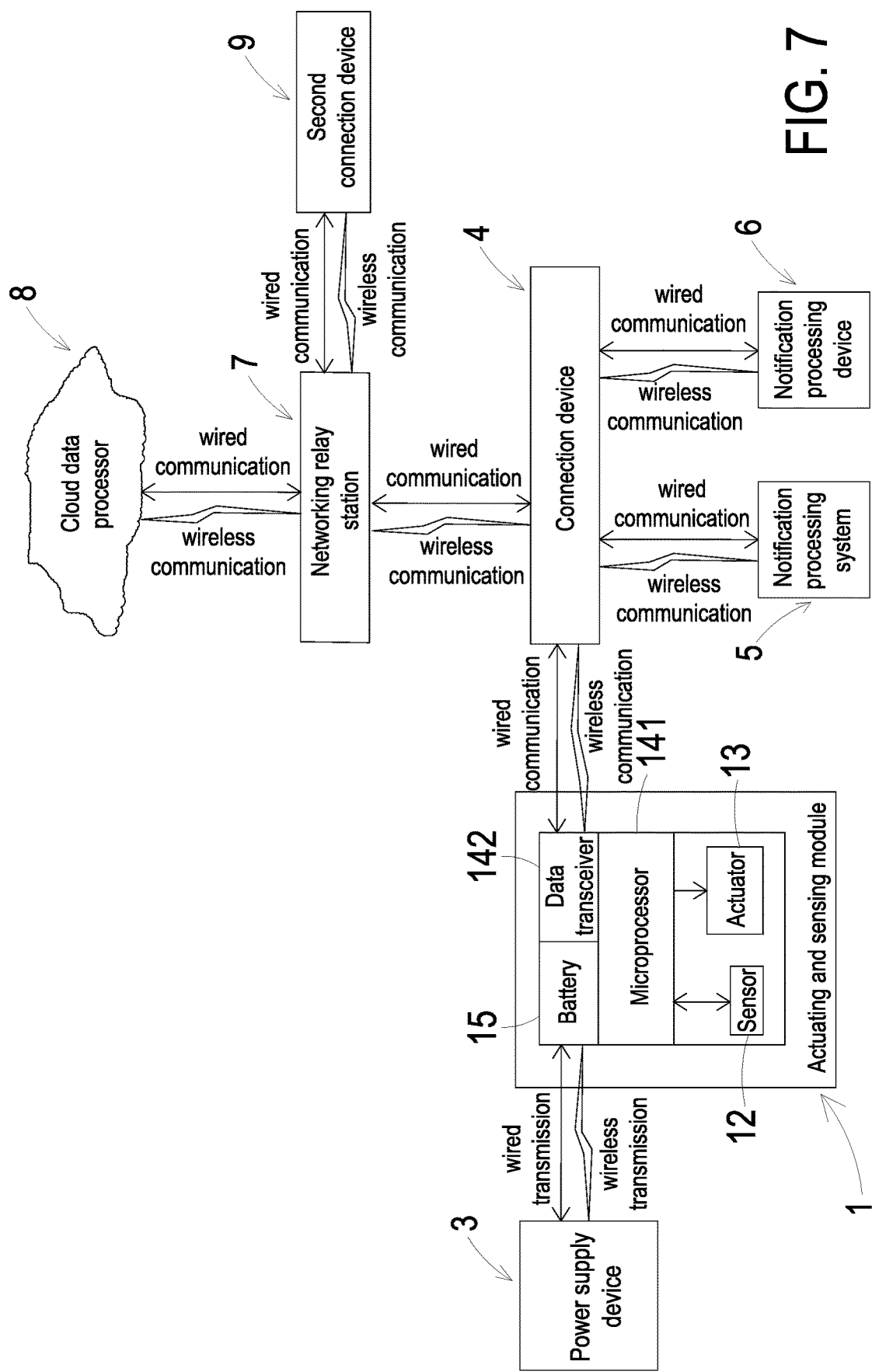
FIG. 7 schematically illustrates the architecture of a driving and information transmitting system according to an embodiment of the present disclosure.

FIG. 7 schematically illustrates the architecture of a driving and information transmitting system according to an embodiment of the present disclosure. The battery 15 of the actuating and sensing module 1 is used to store energy and output energy. The battery 15 transfers the energy to the sensor 12 and the actuator 13 for powering the sensor 12 and the actuator 13. In an embodiment, the battery 15 is externally connected to a power supply device 3 to receive the energy from the power supply device 3. In an embodiment, the power supply device 3 may transfer the energy to the battery 15 through a wireless transmission path. For example, the power supply device 3 is a charger with a wireless charging component (or an inductive charging component), and the power supply device 3 transfers the energy to the battery 15 through a wireless transmission path. For example, the power supply device 3 is a chargeable battery with a wireless charging component (or an inductive charging component), and thus the power supply device 3 may transfer the energy to the battery 15 through the wireless transmission path. In another embodiment, the power supply device 3 is a portable electronic device with wireless charging/discharging function (e.g., a mobile phone with a wireless charging component (or an inductive charging component)), and thus the power supply device 3 may transfer the energy to the battery 15 through the wireless transmission path.

The driving-and-transporting controller 14 of the actuating and sensing module 1 includes a microprocessor 141 and a data transceiver 142. The sensor 12 is used for monitoring the environment to acquire a monitored data. The driving-and-transporting controller 14 processes and calculates the monitored data and controls the actuator 13. The data transceiver 142 can receive or transmit data. The microprocessor 141 receives the monitored data from the sensor 12 and processes and converts the monitored data into an output data. The data transceiver 142 receives the output data and transmits the output data to a connection device 4. After that, the connection device 4 may display or store the information carried in the output data or transfer the information carried in the output data to a storage device to be stored and processed. In an embodiment, the connection device 4 is in communication with a notification processing system 5 to actively (e.g., directly notify) or passively (e.g., in response to the operation by a user acquiring the output data) enable an air quality notification mechanism. For example, an instant air quality map informs people to avoid away or wear masks. In another embodiment, the connection device 4 is in communication with a notification processing device 6 to actively (e.g., directly notify) or passively (e.g., in response to the operation by a user acquiring the output data) enable an air quality processing mechanism. For example, an air cleaner or an air-conditioner is enabled to clean the air.

In an embodiment, the connection device 4 is a display device with a wired communication module (e.g., a desktop computer). In another embodiment, the connection device 4 is a display device with a wireless communication module (e.g., a notebook computer). In another embodiment, the connection device 4 is a portable electronic device with a wireless communication module (e.g., a mobile phone). The wired communication module may have an RS485 communication port, an RS232 communication port, a Modbus communication port or a KNX communication port for wired communication. The wireless communication module may perform a wireless communication through a Zigbee communication technology, a Z-wave communication technology, an RF communication technology, a Bluetooth communication technology, a Wifi communication technology or an EnOcean communication technology.

The driving and information transmitting system further includes a networking relay station 7 and a cloud data processor 8. The connection device 4 is used to transmit the output data to the networking relay station 7. Then, the output data is transmitted from the networking relay station 7 to the cloud data processor 8 to be stored and processed. After the output data is processed by the cloud data processor 8, the cloud data processor 8 issues a notification signal to the networking relay station 7. Then, the networking relay station 7 transmits the notification signal to the connection device 4. According to the notification signal, the notification processing system 5 connected with the connection device 4 enables an air quality notification mechanism. Alternatively, the notification processing device 6 connected with the connection device 4 enables an air quality processing mechanism.

In an embodiment, the connection device 4 issues a control command to the actuating and sensing module 1 so as to control the operation of the actuating and sensing module 1. Similarly, the control command may be transmitted to the data transceiver 142 through wired communication or wireless communication. Then, the control command is transmitted to the microprocessor 141 to control the sensor 12 and the actuator 13 to perform the sensing operation and enable the actuator 13.

In an embodiment, the driving and information transmitting system further includes a second connection device 9 for issuing a control signal. After the second connection device 9 issues the control command to the cloud data processor 8 through the networking relay station 7, the control command is transmitted from the cloud data processor 8 to the connection device 4 through the networking relay station 7, so that the connection device 4 issues the control command to the data transceiver 142. Then, the control command is transmitted to the microprocessor 141. According to the control command, the microprocessor 141 controls the sensor 12 to perform the sensing operation and enables the actuator 13. In an embodiment, the second connection device 9 is a device with a wired communication module. In another embodiment, the second connection device 9 is a device with a wireless communication module. In another embodiment, the second connection device 9 is a portable electronic device with a wireless communication module, but not limited thereto.

From the above descriptions, the present disclosure provides a device equipped with the actuating and sensing module to monitor the environment, thereby a portable device is provided to monitor the air quality. The actuator is used to increase the flow rate of fluid and provide the flow of fluid stably and uniformly. Since the sensor is provided with the flow of the fluid stably and uniformly, the response time of the sensor to the fluid is largely reduced and the fluid is monitored with precision. Moreover, after monitored data is generated by the actuating and sensing module and processed into output data, the output data is transmitted to the connection device. The output data is displayed, stored and transmitted by the connection device. Consequently, the purpose of immediately displaying the output data and issuing the notification signal are achieved. Moreover, the output data can be transmitted to a cloud database. Consequently, the purpose of constructing and managing the data can be achieved. Moreover, in response to the output data received from the cloud database, an air quality notification mechanism and an air quality processing mechanism are enabled to remove the pollutants in the air.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A device, comprising:
    a main body having a length in a range between 0.2 mm and 6 mm, a width in a range between 0.1 mm and 5.5 mm, and a height in a range between 0.1 mm and 2.5 mm; and
    at least one actuating and sensing module disposed in the main body, the at least one actuating and sensing module comprising a carrier, at least one sensor, at least one actuator, a driving-and-transporting controller, a battery and a monitoring chamber, wherein the at least one sensor, the at least one actuator, the driving-and-transporting controller and the battery are disposed on the carrier, and the at least one sensor and the at least one actuator are disposed in the monitoring chamber, wherein the actuator is disposed on one lateral side of the at least one sensor and has at least one fluid channel, wherein the at least one actuator is enabled to transport fluid, so that the fluid flows through the at least one fluid channel toward the at least one sensor, and the at least one sensor measures the fluid received therethrough.

2. The device according to claim 1, wherein a ratio of the width of the main body to the height of the main body is in a range between 0.04 and 55.

3. The device according to claim 1, wherein the monitoring chamber has an inlet passage and an outlet passage, and the main body has an intake opening and a discharge opening, wherein the inlet passage is spatially corresponding to the intake opening of the main body, and the outlet passage is spatially corresponding to the discharge opening of the main body.

4. The device according to claim 3, wherein the inlet passage is covered by a first protective film, and the outlet passage is covered by a second protective film, wherein the first protective film and the second protective film are spatially corresponding to the intake opening and the discharge opening of the main body, respectively, for filtering the fluid passing therethrough in a waterproof and dustproof manner.

5. The device according to claim 3, wherein the at least one sensor is disposed spatially corresponding to the inlet passage, and the at least one actuator is disposed spatially corresponding to the outlet passage.

6. The device according to claim 1, wherein the at least one sensor comprises at least one selected from the group consisting of a gas sensor, an oxygen sensor, a carbon monoxide sensor, a carbon dioxide sensor, a liquid sensor, a temperature sensor, a humidity sensor, an ozone sensor, a particulate sensor, a volatile organic compound sensor, a light sensor, a bacterial sensor, a virus sensor, a microorganism sensor, and a combination thereof.

7. The device according to claim 1, wherein the at least one actuator is a MEMS pump.

8. The device according to claim 1, wherein the at least one actuator is a piezoelectric pump.

9. The device according to claim 8, wherein the piezoelectric pump comprises:
    a fluid inlet plate having at least one inlet, at least one convergence channel and a central cavity defining a convergence chamber, wherein the at least one inlet allows the fluid to flow in, and wherein the convergence channel is spatially corresponding to the inlet and guides the fluid flowing in the inlet to the convergence chamber;
    a resonance plate having a central aperture and a movable part, wherein the central aperture is spatially corresponding to the convergence chamber and the movable part surrounds the central aperture; and
    a piezoelectric actuating member facing the resonance plate, wherein a gap is formed between the resonance plate and the piezoelectric actuating member to define a first chamber, so that the fluid flowing in the at least one inlet of the fluid inlet plate is converged to the central cavity along the at least one convergence channel and flows into the first chamber through the central aperture of the resonance plate when the piezoelectric actuating member is enabled, whereby the fluid is further transferred through a resonance between the piezoelectric actuating member and the movable part of the resonance plate.

10. The device according to claim 9, wherein the piezoelectric actuating member comprises:

a suspension plate being a square suspension plate and having a first surface, a second surface and a bulge, wherein the suspension plate is permitted to undergo a bending vibration;

an outer frame arranged around the suspension plate;

at least one bracket connected between the suspension plate and the outer frame for elastically supporting the suspension plate; and a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

11. The device according to claim 1, wherein the battery is externally connected to a power supply device to receive energy from the power supply device and store the energy, and the energy is provided to the at least one sensor and the at least one actuator for powering the sensor and the actuator.

12. The device according to claim 11, wherein the power supply device transfers the energy to the battery through a wired transmission path or a wireless transmission path, wherein the battery stores the energy and provides the energy to the at least one sensor to perform a sensing operation and the at least one actuator to perform an actuating operation under control.

13. The device according to claim 1, wherein the driving-and-transporting controller comprises:

a microprocessor configured to process and calculate a monitored data sensed by the at least one sensor and control the at least one actuator, wherein the monitored data sensed by the sensor is processed into an output data by the microprocessor; and a data transceiver configured to receive and transmit data, wherein the data transceiver receives the output data and transmits the output data to a connection device, and the connection device displays, stores and transmits the output data.

14. The device according to claim 13, wherein the connection device is connected with a notification processing system or a notification processing device so as to enable an air quality notification mechanism.

15. The device according to claim 13, wherein the connection device is a display device with a wired communication module, a display device with a wireless communication module or a portable electronic device with a wireless communication module.

16. The device according to claim 13, wherein the output data is transmitted from the connection device to a networking relay station, wherein after the output data is transmitted from the networking relay station to a cloud data processor, the output data is processed by and stored in the cloud data processor.

17. The device according to claim 16, wherein after the output data is processed by the cloud data processor, the cloud data processor issues a notification signal to the networking relay station and then transmits the notification signal to the connection device, wherein the connection device is connected with a notification processing system to enable an air quality notification mechanism.

18. The device according to claim 16, wherein after the output data is processed by the cloud data processor, the cloud data processor issues a notification signal to the networking relay station and then transmits the notification signal to the connection device, wherein the connection device is connected with a notification processing device to enable an air quality processing mechanism.

19. The device according to claim 16, further comprising a second connection device to issue a control command, wherein after the second connection device issues the control command to the cloud data processor through the networking relay station, the control command is transmitted from the cloud data processor to the connection device through the networking relay station, so that the connection device issues the control command to the data transceiver.

\* \* \* \* \*